United States Patent [19]

Redl et al.

[11] 4,359,049
[45] Nov. 16, 1982

[54] APPARATUS FOR APPLYING A TISSUE ADHESIVE ON THE BASIS OF HUMAN OR ANIMAL PROTEINS

[75] Inventors: Heinz Redl, Vienna; Gert Kriwetz, Graz, both of Austria

[73] Assignee: Immuno Aktiengesellschaft fur chemisch-medizinische Produkte, Vienna, Austria

[21] Appl. No.: 246,431

[22] Filed: Mar. 23, 1981

[30] Foreign Application Priority Data

Apr. 2, 1980 [AT] Austria ............................ 1792/80

[51] Int. Cl.³ .................................................. A61M 5/00
[52] U.S. Cl. .................................. 128/218 PA; 128/234
[58] Field of Search .......... 128/218 R, 218 N, 218 M, 128/218 S, 224, 234, 215, 220, 221, 218 P, 218 PA

[56] References Cited

U.S. PATENT DOCUMENTS

| 2,112,160 | 3/1938 | Johnson | 128/234 |
|---|---|---|---|
| 3,016,897 | 1/1962 | Kendrick | 128/218 R |
| 3,223,083 | 12/1965 | Cobey | 128/92 R |
| 3,467,096 | 9/1969 | Horn | 128/218 R |
| 3,572,336 | 3/1971 | Hershberg | 128/218 R |
| 3,746,216 | 7/1973 | Frederick | 128/218 M |
| 4,040,420 | 8/1977 | Speer | 128/218 M |
| 4,109,653 | 8/1978 | Kozam et al. | 128/218 R |

FOREIGN PATENT DOCUMENTS

| 137660 | 10/1901 | Fed. Rep. of Germany . |
| 562328 | 1/1931 | Fed. Rep. of Germany . |
| 1491877 | 5/1969 | Fed. Rep. of Germany . |
| 429811 | 10/1911 | France . |
| 440425 | 7/1912 | France . |
| 1054173 | 2/1954 | France . |
| 1051010 | 9/1955 | France ............................ 128/218 M |
| 539551 | 9/1973 | Sweden . |

Primary Examiner—John D. Yasko
Attorney, Agent, or Firm—Brumbaugh, Graves, Donohue & Raymond

[57] ABSTRACT

An arrangement for applying a tissue adhesive on the basis of human or animal proteins for seamlessly or seam-supportingly connecting human or animal tissue or organ parts, sealing wounds, stopping bleedings and the like, which tissue adhesive is formed in situ by bringing together solutions of the proteins and of clot-promoting coagulation factors, includes a holding device for a plurality of syringe bodies ending in coni. In order to achieve a reliable mixing of the tissue adhesive components by single-hand operation with a premature hardening of the components prior to reaching the laceration site being prevented, the coni of the individual syringe bodies are connected by a collecting head having separated conveying channels for the components of the tissue adhesive emerging from the coni. A common actuating device is provided for the plungers of all syringe bodies.

6 Claims, 5 Drawing Figures

U.S. Patent     Nov. 16, 1982     4,359,049
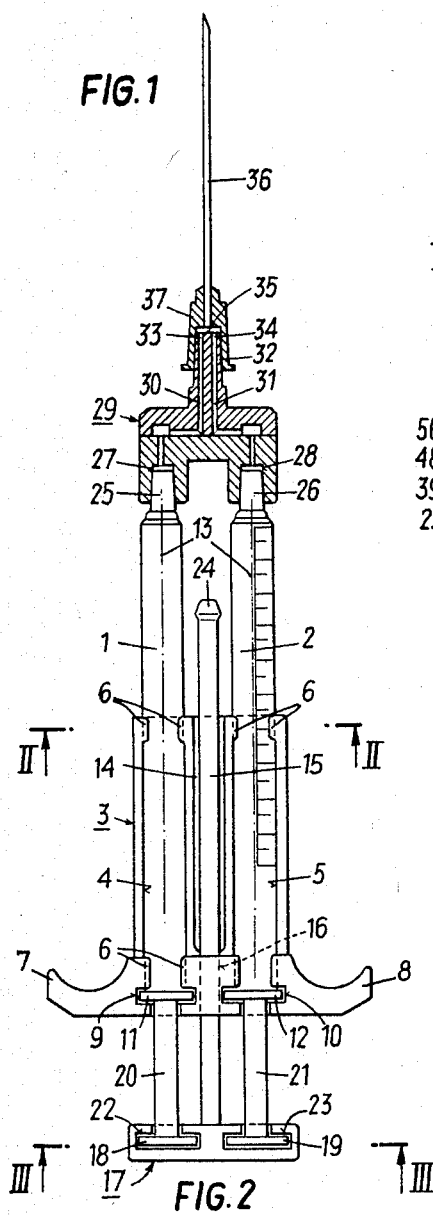
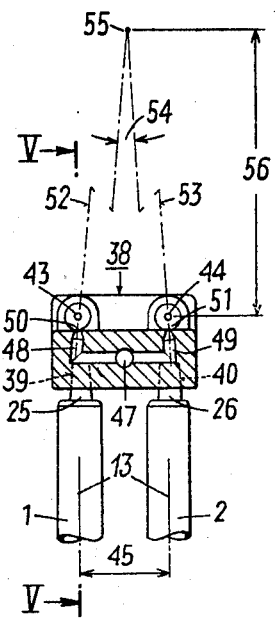
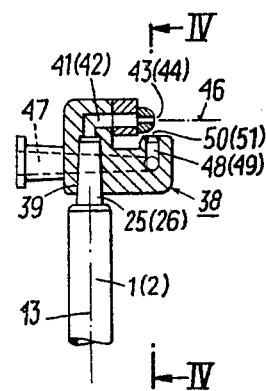
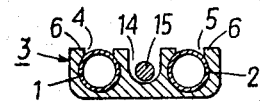
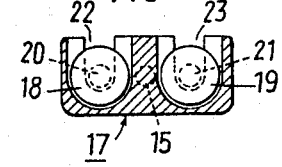

APPARATUS FOR APPLYING A TISSUE ADHESIVE ON THE BASIS OF HUMAN OR ANIMAL PROTEINS

BACKGROUND OF THE INVENTION

The invention relates to an apparatus for applying a tissue adhesive on the basis of human or animal proteins for seamlessly or seam-supportingly connecting human or animal tissue or organ parts, for sealing wounds, stopping bleedings and the like, which tissue adhesive is formed in situ by bringing together solutions of the proteins and of clot-promoting coagulation factors, which apparatus comprises a holding means for a plurality of syringe bodies ending in coni, advantageously standardized one-way syringe bodies of synthetic material.

When using a tissue adhesive of the defined kind, a solution containing factor XIII and fibrinogen is mixed with a solution containing thrombin and is applied onto the laceration site to be adhered or protected. Known modes of application consist in applying the one solution onto the site of adhesion and coating the same with the other solution, or premixing the two solutions in a mixing vessel or also on a drop tray, drawing it into a syringe and then applying it onto the site to be adhered.

Both methods have disadvantages: With the first method a hardening of the surface will occur prematurely due to the different viscosities of the two solutions, before an intensive mixing has taken place. The realization of the second method requires a great skill of the medical personnel, since the hardening of the adhesive takes place soon after the two solutions are combined. Bringing together the components, mixing them, drawing them in a syringe, and applying them onto the site to be adhered have to be effected within few seconds. This method therefore is limited to a few fields of application only.

An arrangement of the initially-defined kind is known from U.S. Pat. No. 3,223,083. The syringe bodies are seized by a clamp-like holding means, and the coni of the syringe bodies are inserted in a Y-piece. In this Y-piece the two components of the tissue adhesive are mixed, wherein a hardening of the tissue adhesive in the Y-piece in the event of a short-time interruption in the injection procedure is inevitable. Therefore, after such an interruption the Y-piece must to be exchanged, which is cumbersome.

SUMMARY OF THE INVENTION

The invention aims at avoiding the disadvantages and difficulties described and has as its object to provide an apparatus of the initially-defined kind, by which the application of the adhesive components can be effected simultaneously by a single-hand operation of the apparatus, with a reliable mixing being obtained and a premature hardening of the components prior to reaching the laceration site being prevented.

This object is achieved according to the invention in that the coni of the individual syringe bodies are connected by a collecting head including separated conveying channels for each of the components of the tissue adhesive leaving the respective coni, a mixing needle being slipable onto the collecting head if desired, and that a common actuating means is provided for the plungers of all the syringe bodies. For the apparatus, there may be used standardized one-way apparatus parts that are commonly available, e.g. one-way syringe bodies and plungers as well as standardized needles, and which are commercially available in sterilized packings and are in the stock of a physician's instrumentarium.

For the purpose of better handling, the common actuating means for the syringe plungers is guided along a guide rod penetrating the holding means.

Suitably, the mouths of the conveying channels are arranged in a closely adjacent manner on the end side of one slip-on conus of the collecting head.

Advantageously, the mouths of the conveying channels of the collecting head are situated in the region of the outlets of supply channels for sterile gases which are laid at an angle to one another.

According to a further advantageous embodiment, the axes of the outlets of the supply channels are directed at an acute angle to one another, the angle vertex being at a distance, preferably at a distance of 10 to 20 cm, in front of the mouths of the conveying channels.

BRIEF DESCRIPTION OF THE DRAWINGS

The apparatus according to the invention will now be explained in more detail by way of two embodiments with reference to the accompanying drawing, wherein:

FIG. 1 is a partially sectioned side view of the apparatus according to a first embodiment;

FIG. 2 is a section along line II—II of FIG. 1;

FIG. 3 is a section along line III—III of FIG. 1; and

FIGS. 4 and 5 are partially sectioned illustrations of a second embodiment, FIG. 4 being a section along line IV—IV of FIG. 5, and FIG. 5 being a section along line V—V of FIG. 4.

DESCRIPTION OF EXEMPLARY EMBODIMENTS

Two syringe bodies are denoted by 1 and 2, one of which serves for accommodating a solution containing thrombin and the other of which serves for accommodating a solution containing factor XIII and fibrinogen. The syringe bodies 1, 2 suitably are designed as standardized one-way syringe bodies of synthetic material. They are commonly inserted in a holding device 3. The holding device 3 has two U-shaped grooves 4, 5, each of which on its end is provided with nipples 6 overlapping the biggest cross section of each groove, so that the syringe bodies 1, 2, which are inserted in the grooves 4, 5 from above, will snap in, being held fast in the grooves by the nipples 6. On the end of the holding device that comprises two lateral finger grips 7, 8 U-shaped enlargements 9, 10 of the grooves are provided into which the flange ends 11, 12 of the syringe bodies project, so that the syringe bodies 1, 2 are fixed in the holding device 3 also in the direction of their respective longitudinal axis 13.

In the middle between the two U-shaped grooves 4, 5 a recess 14 is provided for a guide rod 15, which, in the region of the end of the holding device 3 that comprises the finger grips 7, 8, passes over into a bore 16 penetrating this end. The guide rod 15 is connected in one piece with an actuating means 17, into which the thumb yokes 18, 19 of the plungers 20, 21 of the syringe bodies 1, 2 are inserted. The thumb yokes 18, 19 of the plungers 20, 21 are each inserted in a U-shaped recess 22, 23 of the actuating means 17. The guide rod 15 on its front end comprises an enlargement 24 so that it will not slide out of the bore 16 of the holding device 3.

The two coni 25, 26 of the syringe bodies project into plug-in coni 27, 28 of a collecting head 29 and are connected by this collecting head. Within the collecting head 29 a separate conveying channel 30, 31 leads from each plug-in conus 27, 28 to a slip-on conus head 32 provided on the collecting head. The mouths 33, 34 of the conveying channels 30, 31 are provided on the end side 35 of this slip-on conus head in a closely adjacent manner. A mixing needle 36, which is provided with a standardized plug-in conus 37 on its rear end, can be slipped onto the slip-on conus head 32.

By pressing the thumb onto the actuating means 17, predetermined volumina simultaneously leave the two syringe bodies 1, 2. Due to the slight distance of the mouths 33, 34 of the conveying channels 30, 31, an immediate contact of the two solutions occurs, the mixing effect being an optimal one. The application of one syringe charge can be effected both intermittently and continuously. Used syringe bodies 1, 2 and the mixing needle 36 can be exchanged rapidly and the entire apparatus can easily be sterilized, if desired. The single-hand operation and the automatic dosing of the two solutions at the desired ratio constitute a substantial operational facilitation. If a mixing needle 36 is used, the mixture will be of a particular intensity, adherings of maximum strengths thus being feasible. If the application of the tissue adhesive is interrupted, the mixing needle 36 has to be removed and replaced by a new one. The collecting head 29, however, can be used further. The arrangement described allows for an application of the tissue adhesive in nearly all fields.

The embodiment illustrated in FIGS. 4 and 5 makes possible the spraying of the tissue adhesive onto a surface to be adhered or sealed. With this embodiment, the collecting head is designed as a spraying head 38. It comprises two separated conveying channels 41, 42, departing from the plug-in coni 39, 40, whose mouths 43, 44 are arranged at a distance approximately corresponding to the distance 45 of the syringe bodies 1, 2. The outlet direction 46 of the solutions from the mouths 43, 44 is approximately at a right angle to the longitudinal direction 13 of the syringe bodies 1, 2.

In addition to the conveying channels 41, 42 the collecting or spraying head 38 comprises a supply channel 47 for a sterile gas, for instance compressed air, which divides into two branches 48, 49 within the collecting head. The outlets 50, 51 of these two supply channels 48, 49 are arranged in the region of the mouths 43, 44 of the conveying channels 41, 42. The axes 52, 53 of the outlet openings 50, 51 are directed at an approximately right angle to the outlet direction 46 of the solutions, the axes 52, 53 of the outlets being directed toward each other at an acute angle 54 and the angle vertex 55 lying at a distance 56 of about 10 to 20 cm in front of the mouths of the conveying channels.

With this embodiment the dosing of the solution is effected also with the help of the actuating means, which is designed in the same manner as the actuating means of the embodiment illustrated in FIG. 1. The application of the tissue adhesive can be interrupted without exchanging the spraying means 38. The two spraying cones unite at a distance of about 10 to 20 cm, rapidly forming a thin uniform adhesive film on the surface to be adhered or sealed. The mixing of the components is to be regarded as optimal also with this embodiment. Additionally, this embodiment has the advantage that, prior to the application proper, the adhesion site can be dried, i.e. body liquid can be blown off by compressed air, a better adherence of the adhesive thus being obtained. By the good dosability of the tissue adhesive, the operation with this embodiment of the apparatus is particularly economical.

The spraying head allows for an application of the tissue adhesive to larger areas. Particularly preferred fields of application are blood stoppings, wound sealings, burns, skin transplantations, and the spraying out of body cavities.

What we claim is:

1. In an apparatus for applying a tissue adhesive on the basis of human or animal proteins to be used for seamlessly or seam-supportingly connecting human or animal tissue or organ parts, for sealing wounds, for stopping bleedings and the like, said tissue adhesive being formed in situ by bringing together at least two components comprised of solutions of proteins and clot-promoting coagulation factors, and of the type including a plurality of standardized one-way syringe bodies of synthetic material, said syringe bodies accommodating plungers and ending in coni, and a holding means provided for said plurality of syringe bodies, the improvement which comprises a collecting head connecting said coni of said syringe bodies, separated conveying channels provided in said collecting head for said at least two components emerging from the respective one of said coni, a guide rod penetrating said holding means, and a common actuating means being guided along said guide rod provided for the plungers of said syringe bodies.

2. An apparatus as set forth in claim 1, further comprising a mixing needle to be slipped onto said collecting head.

3. An apparatus as set forth in claim 1, further comprising a slip-on cone provided on said collecting head and having an end side at which said separated conveying channels have their mouths closely adjacently arranged.

4. An apparatus as set forth in claim 1, further comprising supply channels for sterile gases laid at an angle to one another and having outlets in the region of which said separated conveying channels of said collecting head have their mouths.

5. An apparatus as set forth in claim 4, wherein said outlets of said supply channels have axes directed at an acute angle to one another so as to provide an angle vertex, lying at a distance in front of the mouths of said separated conveying channels.

6. An apparatus as set forth in claim 5, wherein said angle vertex lies at a distance of 10 to 20 cm in front of the mouths of said separated conveying channels.

* * * * *